(12) United States Patent
Leven

(10) Patent No.: US 10,179,234 B2
(45) Date of Patent: Jan. 15, 2019

(54) DISTALLY REINFORCED LEAD AND METHODS OF MAKING AND USING

(71) Applicant: BOSTON SCIENTIFIC NEUROMODULATION CORPORATION, Valencia, CA (US)

(72) Inventor: Jacob B. Leven, Huntington Beach, CA (US)

(73) Assignee: Boston Scientific Neuromodulation Corporation, Valericia, CA (US)

( * ) Notice: Subject to any disclaimer, the term of this patent is extended or adjusted under 35 U.S.C. 154(b) by 813 days.

(21) Appl. No.: 14/091,863

(22) Filed: Nov. 27, 2013

(65) Prior Publication Data

US 2014/0155969 A1 Jun. 5, 2014

Related U.S. Application Data

(60) Provisional application No. 61/732,784, filed on Dec. 3, 2012.

(51) Int. Cl.
*A61N 1/00* (2006.01)
*A61N 1/05* (2006.01)

(52) U.S. Cl.
CPC .................... *A61N 1/0551* (2013.01)

(58) Field of Classification Search
CPC ......... A61N 1/05; A61N 1/375; A61N 1/3787
USPC .................. 607/116, 115, 119; 604/523–528
See application file for complete search history.

(56) References Cited

U.S. PATENT DOCUMENTS

| | | | |
|---|---|---|---|
| 5,728,148 A * | 3/1998 | Bostrom | A61N 1/056 600/373 |
| 5,755,760 A * | 5/1998 | Maguire | A61B 5/0422 607/122 |
| 5,833,604 A * | 11/1998 | Houser | A61B 18/1492 600/373 |
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,244,150 B1 | 7/2007 | Brase et al. | |
| 7,437,193 B2 | 10/2008 | Parramon et al. | |
| 7,672,734 B2 | 3/2010 | Anderson et al. | |
| 7,761,165 B1 | 7/2010 | He et al. | |
| 7,949,395 B2 | 5/2011 | Kuzma | |
| 7,974,706 B2 | 7/2011 | Moffitt et al. | |
| 8,175,710 B2 | 5/2012 | He | |

(Continued)

*Primary Examiner* — Christopher D Koharski
*Assistant Examiner* — Philip C Edwards
(74) *Attorney, Agent, or Firm* — Lowe Graham Jones PLLC; Bruce E. Black

(57) ABSTRACT

An electrical stimulation lead includes a lead body that defines a central lumen extending along the longitudinal length of the lead body. The stimulation lead includes electrodes disposed along the distal end of the lead body, terminals disposed along the proximal end of the lead body, and conductors. Each conductor electrically couples at least one of the electrodes to at least one of the terminals. The stimulation lead also includes a tubular reinforcing member disposed in the central lumen of the lead body within a portion of the distal end of the lead body or at least one reinforcing member disposed upon the distal end of the lead body proximal of the plurality of electrodes. The reinforcing member stiffens a portion of the distal end of the lead body.

16 Claims, 9 Drawing Sheets

(56) References Cited

U.S. PATENT DOCUMENTS

| | | |
|---|---|---|
| 8,224,450 B2 | 7/2012 | Brase |
| 8,364,278 B2 | 1/2013 | Pianca et al. |
| 2003/0009207 A1* | 1/2003 | Paspa .................. A61N 1/0529 607/116 |
| 2007/0150036 A1 | 6/2007 | Anderson |
| 2010/0057174 A1* | 3/2010 | Harrison ................ A61L 29/04 607/115 |

* cited by examiner

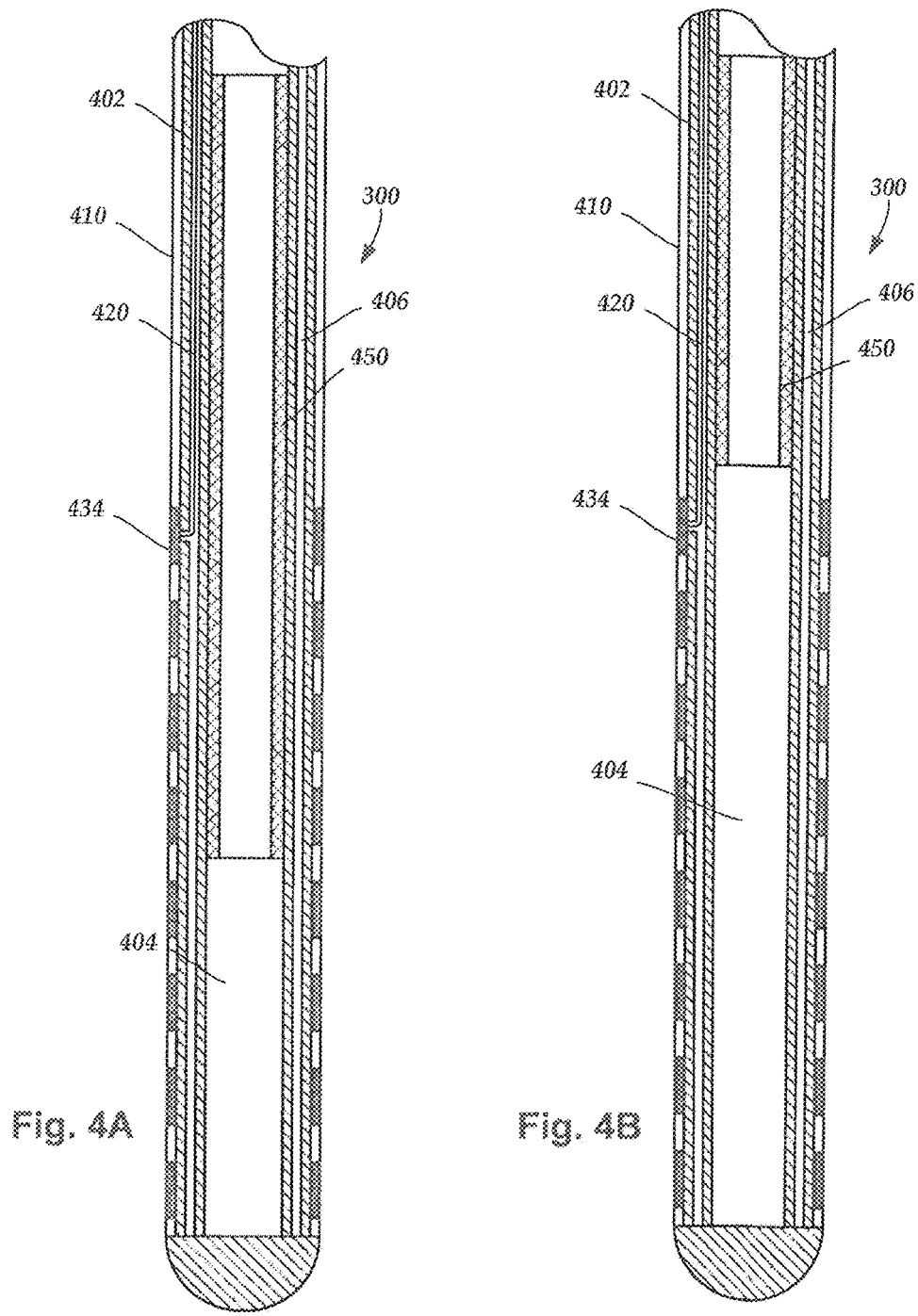

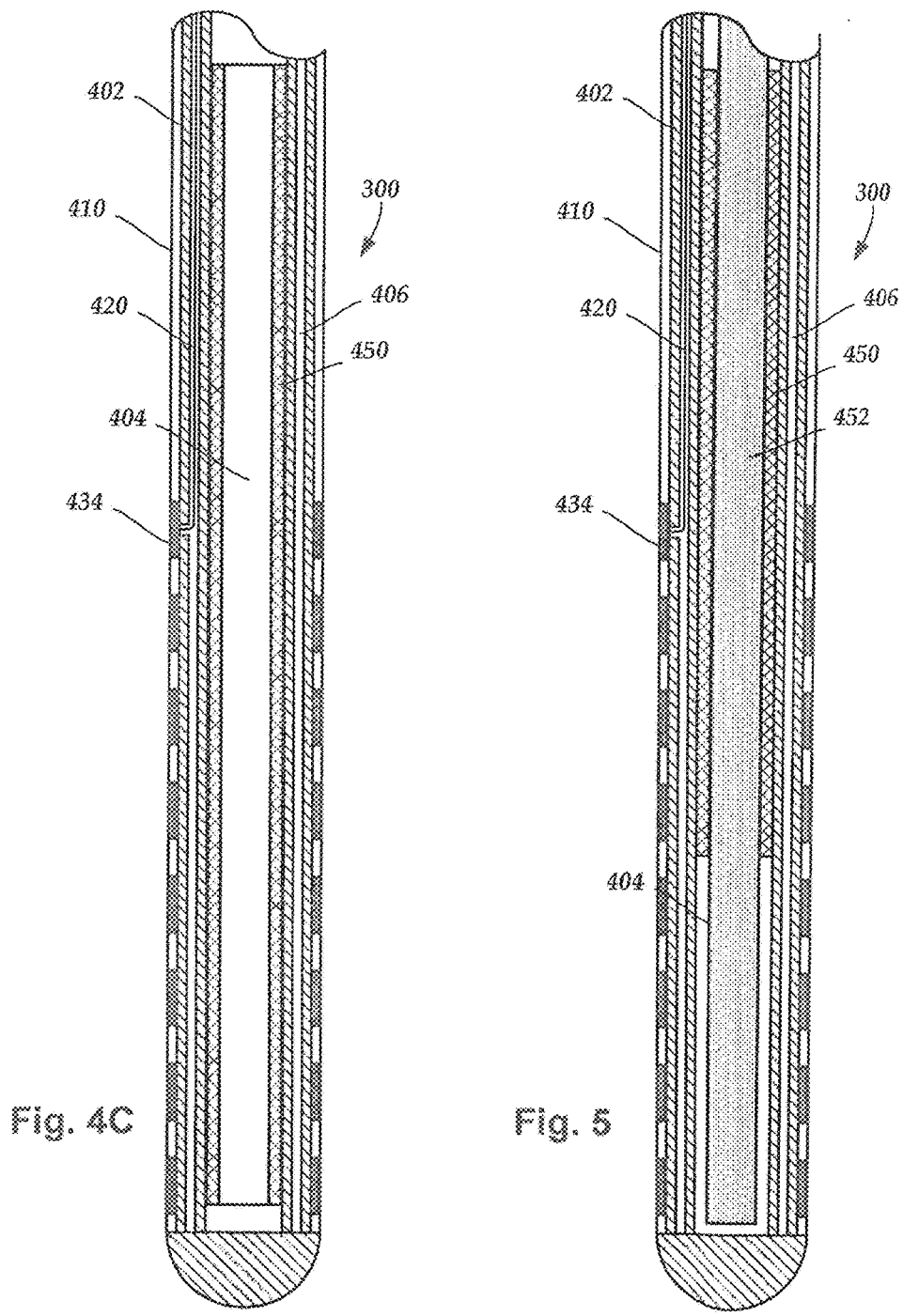

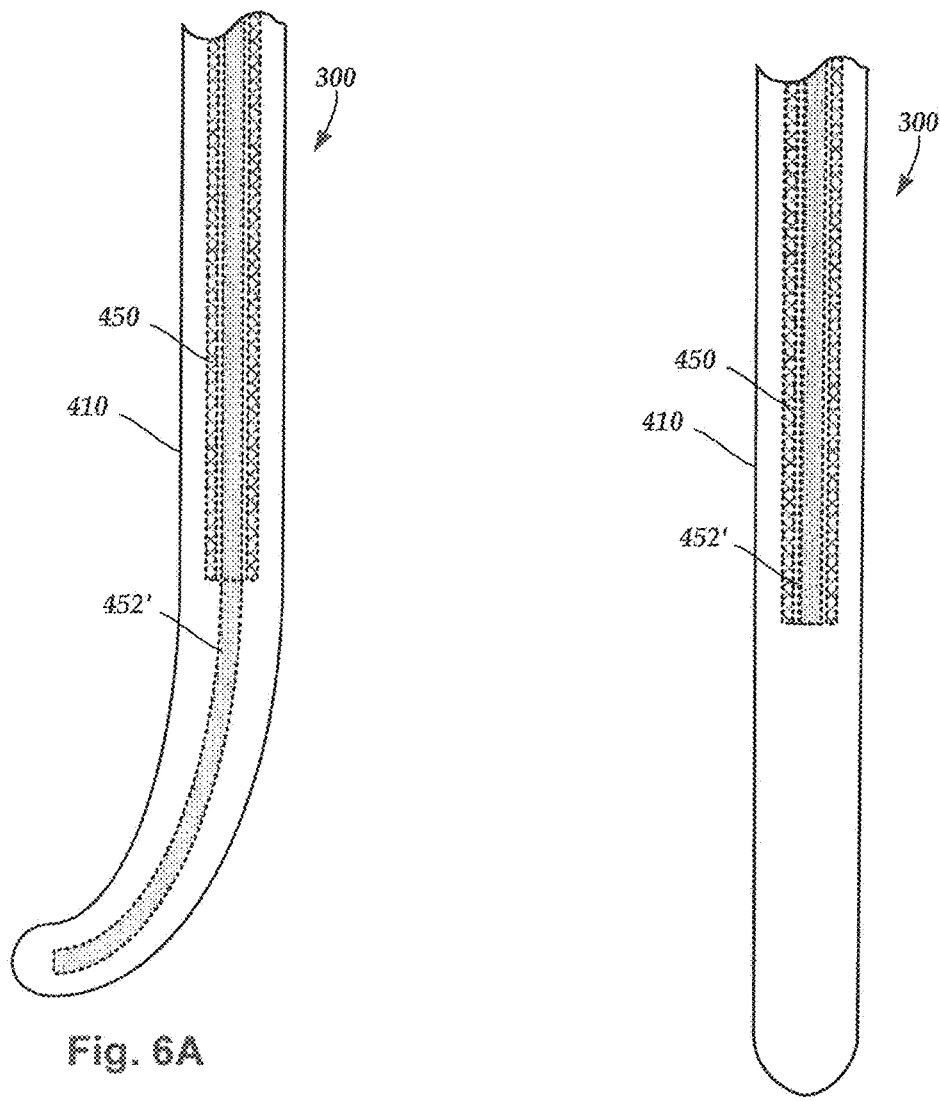

DISTALLY REINFORCED LEAD AND METHODS OF MAKING AND USING

CROSS-REFERENCE TO RELATED APPLICATIONS

This application claims the benefit under 35 U.S.C. § 119(e) of U.S. Provisional Patent Application Ser. No. 61/732,784 filed Dec. 3, 2012, which is incorporated herein by reference.

FIELD

The present invention is directed to the area of implantable electrical stimulation systems and methods of making and using the systems. The present invention is also directed to implantable electrical stimulation leads having one or more distal reinforcing elements, as well as methods of making and using the leads and electrical stimulation systems.

BACKGROUND

Invasive electrical stimulation systems have proven therapeutic in a variety of diseases and disorders. For example, implantable stimulation systems can be implanted in the spinal cord to treat chronic pain syndromes and in the brain to treat refractory chronic pain syndromes, movement disorders, and epilepsy. Peripheral nerve stimulation systems may be used to treat chronic pain syndrome and incontinence. In some cases, paralyzed extremities in spinal cord injury patients may be treated using functional electrical stimulation. Moreover, electrical stimulation systems can be implanted subcutaneously to stimulate subcutaneous tissue including subcutaneous nerves such as the occipital nerve.

In general, a stimulator includes a control module (with a pulse generator), one or more leads, and an array of stimulator electrodes mounted on the lead body. The stimulator electrodes are placed in contact with or near the nerves, muscles, or other tissue to be stimulated. The pulse generator in the control module generates electrical pulses that are delivered through the electrodes to body tissue.

To provide effective stimulation, the electrodes should face the desired body part or tissue to be stimulated. For example, in spinal cord stimulation (SCS), the neurosurgeons should know the orientation of the distal end of the lead supporting the stimulating array of the lead. During deployment, however, the lead may twist or turn such that it may not be deployed in the desired orientation.

In at least some instances, linear spinal cord stimulation (SCS) leads are implanted into the epidural space via an epidural needle. A lead that is incorrectly placed may result in ineffective stimulation. Subsequent surgery may be necessary to re-implant the stimulation system in the desired position.

SUMMARY

One embodiment is an electrical stimulation lead including a lead body having a distal end, a proximal end, and a longitudinal length. The lead body defines a central lumen extending along the longitudinal length of the lead body. The stimulation lead includes a number of electrodes disposed along the distal end of the lead body, a number of terminals disposed along the proximal end of the lead body, and multiple conductors. Each conductor electrically couples at least one of the electrodes to at least one of the terminals. The stimulation lead also includes a tubular reinforcing member disposed in the central lumen of the lead body within a portion of the distal end of the lead body. The reinforcing member extends proximal of the electrodes. The reinforcing member is configured and arranged to stiffen a portion of the distal end of the lead body in which the reinforcing member resides.

Another embodiment is an electrical stimulation lead including a lead body having a distal end, a proximal end, and a longitudinal length. The lead include a number of electrodes disposed along the distal end of the lead body, a number of terminals disposed along the proximal end of the lead body, and multiple conductors. Each conductor electrically couples at least one of the electrodes to at least one of the terminals. The lead also includes at least one reinforcing member disposed upon a portion of the distal end of the lead body proximal of the electrodes. The reinforcing member is configured and arranged to stiffen a portion of the distal end upon which the at least one reinforcing member is disposed.

Either of the electrical stimulation leads described above can be combined with a control module and an optional lead extension to form an electrical stimulation system.

A further embodiment is a method of implanting an electrical stimulation lead. The method may include providing the first of the electrical stimulation leads described above and inserting the stylet into the central lumen of the lead body and through the tubular reinforcing member. The electrical stimulation lead is implanted into a patient using the curved distal end of the stylet to curve at least a portion of the distal end of the electrical stimulation lead and steer the lead to a desired implantation site.

BRIEF DESCRIPTION OF THE DRAWINGS

Non-limiting and non-exhaustive embodiments of the present disclosure are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a lateral cross-section view of a first embodiment of a distal end of a lead with a reinforcing member disposed in the central lumen, according to the invention;

FIG. 4B is a lateral cross-section view of a second embodiment of a distal end of a lead with a reinforcing member disposed in the central lumen, according to the invention;

FIG. 4C is a lateral cross-section view of a third embodiment of a distal end of a lead with a reinforcing member disposed in the central lumen, according to the invention;

FIG. 5 is a lateral cross-section view of a fourth embodiment of a distal end of a lead with a reinforcing member and a stylet disposed in the central lumen, according to the invention;

FIG. 6A is a side view of one embodiment of a distal end of a lead with a reinforcing member and a curving stylet disposed within the central lumen (electrodes are not illustrated in FIG. 6A for clarity), according to the invention;

FIG. 6B is a side view of one embodiment of a distal end of a lead with a reinforcing member and a curving stylet disposed within the central lumen (electrodes are not illustrated in FIG. 6B for clarity), where the curving stylet is retracted into the reinforcing member to straighten the curved portion of the stylet, according to the invention;

DETAILED DESCRIPTION

The present invention is directed to the area of implantable electrical stimulation systems and methods of making and using the systems. The present invention is also directed to implantable electrical stimulation leads having one or more distal reinforcing elements, as well as methods of making and using the leads and electrical stimulation systems.

Suitable implantable electrical stimulation systems include, but are not limited to, at least one lead with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated herein by reference.

Figure 1:
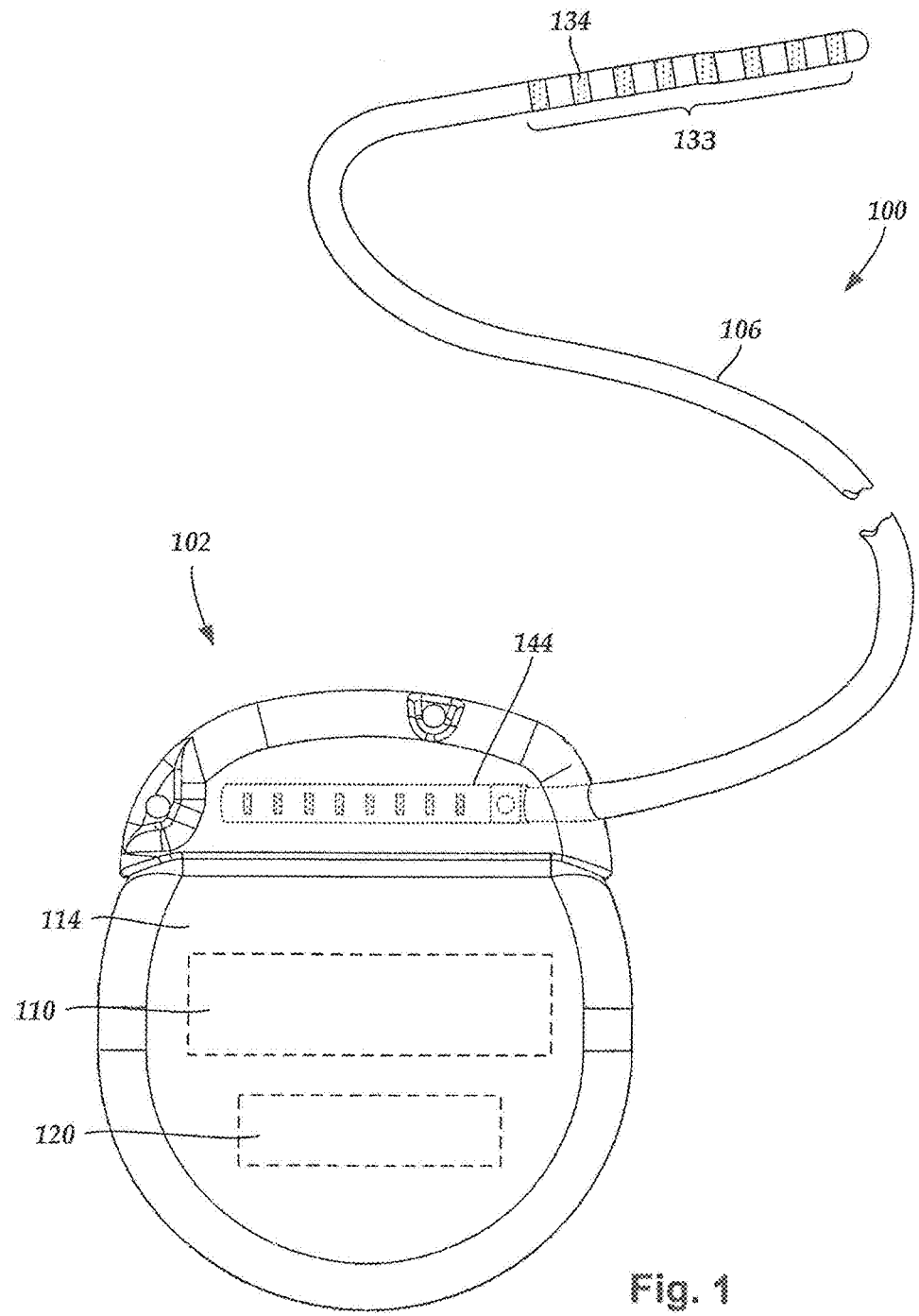
FIG. 1 is a schematic view of one embodiment of an electrical stimulation system, according to the invention.

FIG. 1 illustrates schematically one embodiment of an electrical stimulation system 100. The electrical stimulation system includes a control module 102 (e.g., a stimulator or pulse generator) and at least one lead 106 coupled to the control module 102. Each lead 106 typically includes an array of electrodes 133. The control module 102 typically includes an electronic subassembly 110 and an optional power source 120 disposed in a sealed housing 114. The control module 102 typically includes a connector 144 (FIG. 2A, see also 222 and 250 of FIG. 2B) into which the proximal end of the one or more leads 106 can be plugged to make an electrical connection via conductive contacts 214 (FIG. 2A) on the control module 102 and terminals (e.g., 210 in FIG. 2A and 236 of FIG. 2B) on each of the one or more leads 106. In at least some embodiments, a lead is isodiametric along a longitudinal length of the lead 106. In addition, one or more lead extensions 224 (see FIG. 2B) can be disposed between the one or more leads 106 and the control module 102 to extend the distance between the one or more leads 106 and the control module 102 of the embodiment shown in FIG. 1.

The electrical stimulation system 100 or components of the electrical stimulation system 100, including one or more of the leads 106 and the control module 102, are typically implanted into the body of a patient. The electrical stimulation system 100 can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in the array of electrodes 133 may vary. For example, there can be two, four, six, eight, ten, twelve, fourteen, sixteen, or more electrodes 134. As will be recognized, other numbers of electrodes 134 may also be used.

The electrodes 134 of one or more leads 106 are typically disposed in, or separated by, a non-conductive, biocompatible material such as, for example, silicone, polyurethane, polyetheretherketone ("PEEK"), epoxy, and the like or combinations thereof. The leads 106 may be formed in the desired shape by any process including, for example, molding (including injection molding), casting, and the like. The non-conductive material typically extends from the distal end of the one or more leads 106 to the proximal end of each of the one or more leads 106 and forms, at least in part, the lead body.

Terminals (e.g., 210 in FIG. 2A and 236 of FIG. 2B) are typically disposed at the proximal end of the one or more leads 106 of the electrical stimulation system 100 for connection to corresponding conductive contacts (e.g., 214 in FIG. 2A and 240 of FIG. 2B) in connectors (e.g., 144 in FIGS. 1-2A and 222 and 250 of FIG. 2B) disposed on, for example, the control module 102 (or to conductive contacts on a lead extension, an operating room cable, or an adaptor). Conductor wires (not shown) extend from the terminals (e.g., 210 in FIG. 2A and 236 of FIG. 2B) to the electrodes 134. Typically, one or more electrodes 134 are electrically coupled to a terminal (e.g., 210 in FIG. 2A and 236 of FIG. 2B). In at least some embodiments, each terminal (e.g., 210 in FIG. 2A and 236 of FIG. 2B) is only connected to one electrode 134.

The conductor wires may be embedded in the non-conductive material of the lead 106 or can be disposed in one or more lumens (not shown) extending along the lead 106. In some embodiments, there is an individual lumen for each conductor wire. In other embodiments, two or more conductor wires may extend through a lumen. There may also be one or more lumens (not shown) that open at, or near, the proximal end of the lead 106, for example, for inserting a stylet wire to facilitate placement of the lead 106 within a body of a patient. Additionally, there may also be one or more lumens (not shown) that open at, or near, the distal end of the lead 106, for example, for infusion of drugs or medication into the site of implantation of the one or more leads 106. In at least one embodiment, the one or more lumens may be flushed continually, or on a regular basis, with saline, epidural fluid, or the like. In at least some embodiments, the one or more lumens can be permanently or removably sealable at the distal end.

Figure 2A:
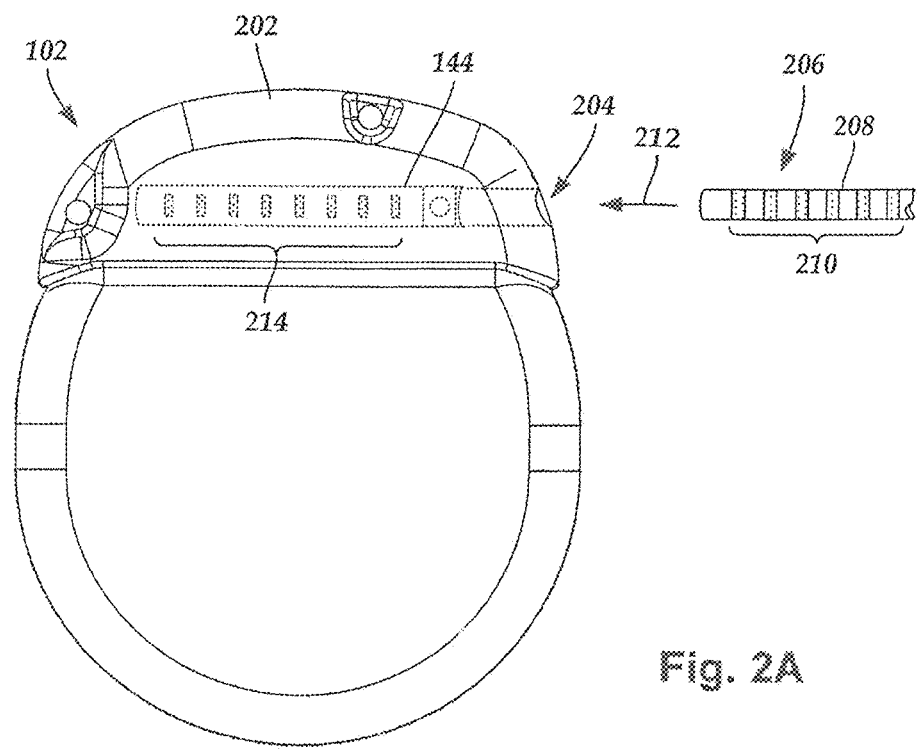
FIG. 2A is a schematic view of one embodiment of a proximal portion of a lead and a control module of an electrical stimulation system, according to the invention.

In at least some embodiments, leads 106 are coupled to connectors disposed on one or more control modules 102. In FIG. 2A, a lead 208 is shown configured and arranged for insertion to the control module 102. The connector 144 includes a connector housing 202. The connector housing 202 defines at least one port 204 into which a proximal end 206 of a lead 208 with terminals 210 can be inserted, as shown by a directional arrow 212. The connector housing 202 also includes a plurality of conductive contacts 214 for each port 204. When the lead 208 is inserted into the port 204, the conductive contacts 214 can be aligned with the terminals 210 on the lead 208 to electrically couple the control module 102 to the electrodes (134 of FIG. 1) disposed along a distal end of the lead 208. Examples of connectors in control modules are found in, for example, U.S. Pat. Nos. 7,244,150 and 8,224,450, which are incorporated herein by reference.

Figure 2B:
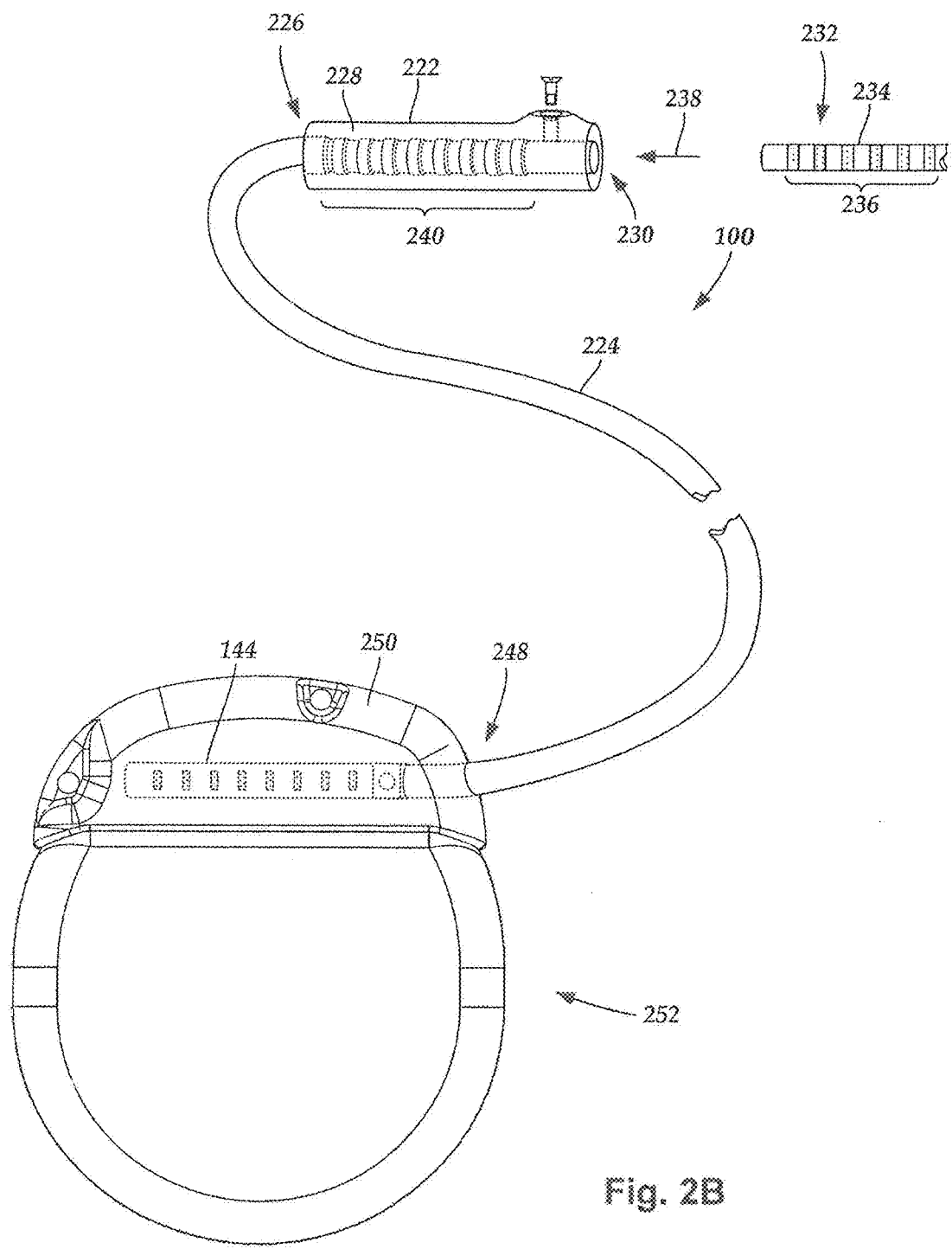
FIG. 2B is a schematic view of one embodiment of a proximal portion of a lead and a lead extension of an electrical stimulation system, according to the invention.

In FIG. 2B, a connector 222 is disposed on a lead extension 224. The connector 222 is shown disposed at a distal end 226 of the lead extension 224. The connector 222 includes a connector housing 228. The connector housing 228 defines at least one port 230 into which a proximal end 232 of a lead 234 with terminals 236 can be inserted, as shown by directional arrow 238. The connector housing 228 also includes a number of conductive contacts 240. When the lead 234 is inserted into the port 230, the conductive contacts 240 disposed in the connector housing 228 can be aligned with the terminals 236 on the lead 234 to electrically couple the lead extension 224 to the electrodes (134 of FIG. 1) disposed at a distal end (not shown) of the lead 234.

In at least some embodiments, the proximal end of a lead extension 224 is similarly configured and arranged as a proximal end of a lead to connect with a control module 102. The lead extension 224 may include a number of conductive wires (not shown) that electrically couple the conductive contacts 240 to a proximal end 248 of the lead extension 224 that is opposite to the distal end 226. In at least some embodiments, the conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a connector disposed in another lead extension. In other embodiments, the proximal end 248 of the lead extension 224 is configured and arranged for insertion into a connector disposed in a control module. As an example, in FIG. 2B the proximal end 248 of the lead extension 224 is inserted into a connector 250 disposed in a control module 252.

Figure 3A:
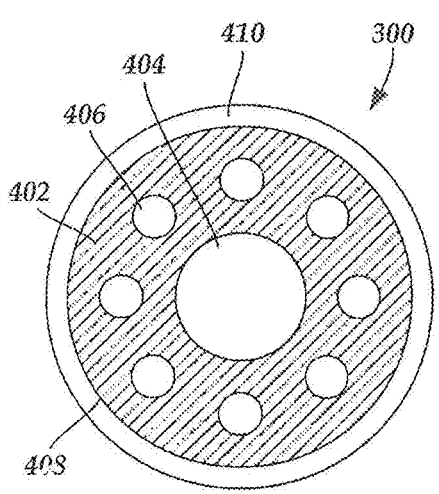
FIG. 3A is a transverse cross-sectional view of one embodiment of the distal portion of the lead of FIG. 1, the lead including a multi-lumen conductor guide that defines a central lumen and a plurality of conductor lumens arranged around the central lumen, according to the invention.

Turning to FIG. 3A, in at least some embodiments, the lead includes a lead body with an elongated multi-lumen conductor guide having one or more conductor lumens (preferably, multiple conductor lumens) arranged about a central lumen. In at least some embodiments, the conductor lumens are arranged about the central lumen such that there are no other lumens extending along the multi-lumen conductor guide between the central lumen and each of the multiple conductor lumens. In some embodiments, each of the conductor lumens is configured and arranged to receive a single conductor. In other embodiments, at least one of the conductor lumens is configured and arranged to receive multiple conductors.

FIG. 3A is a transverse cross-sectional view of one embodiment of a lead 300. The lead 300 includes an elongated multi-lumen conductor guide 402. The multi-lumen conductor guide 402 may extend an entire longitudinal length of the lead 300 from the electrodes 434 (FIG. 4A) to the terminals 210 (FIG. 2A). As shown in FIG. 3A, the multi-lumen conductor guide 402 defines a central or main lumen 404 and a plurality of conductor lumens, such as conductor lumen 406. The conductor lumens 406 can have any suitable cross-sectional shape (e.g., round, oval, rectangular, triangular, or the like).

In at least some embodiments, the plurality of conductor lumens 406 are encapsulated by the multi-lumen conductor guide 402 such that the conductor lumens 406 do not extend to an outer surface 408 of the multi-lumen conductor guide 402. In which case, when conductors (420 in FIG. 3B) are disposed in the conductor lumens 406, the conductors are not exposed along the outer surface 408 of the multi-lumen conductor guide 402. The central lumen 404 and the plurality of conductor lumens 406 can be arranged in any suitable manner. In preferred embodiments, the conductor lumens 406 are disposed in the multi-lumen conductor guide 402 such that the conductor lumens 406 are arranged peripheral to, or generally surround, the central lumen 404. In at least some embodiments, the lead 300 may include one or more outer coatings of material 410 disposed over the outer surface 408 of multi-lumen conductor guide 402.

Figure 3B:
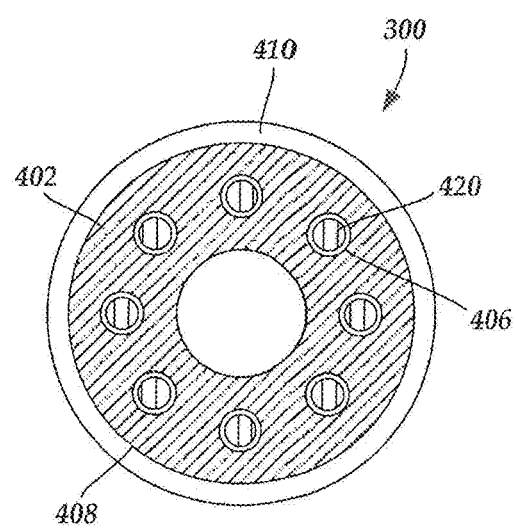
FIG. 3B is a transverse cross-sectional view of one embodiment of conductors disposed in each of a plurality of conductor lumens of the multi-lumen conductor guide of FIG. 3A such that a different single conductor is disposed in each of the conductor lumens, according to the invention.

The plurality of conductor lumens 406 are configured and arranged to receive conductors (420 in FIG. 3B), which electrically couple the electrodes 434 (FIG. 4A) to the terminals 210 (FIG. 2A). FIG. 3B is a transverse cross-sectional view of one embodiment illustrating how each conductor 420 can be disposed in one of the respective conductor lumens 406.

A multi-lumen conductor guide can be formed of any suitable material including, but not limited to, polyurethane, silicone, or silicone-polyurethane copolymer. It will be recognized that the multi-lumen conductor guide need not have the specific form illustrated in FIGS. 3A and 3B and that other conductor guide arrangements can be used including arrangements that permit more than one conductor per lumen or includes fewer conductor lumens (in some instances, a single conductor lumen). In some embodiments, the conductor guide 402 may be formed around the conductors 420 by molding or other methods. In some embodiments, the conductor guide 402 may be formed first and then the conductors 420 may be inserted into the conductor guide 402.

As explained above, a stimulation lead can be implanted into the epidural space using, for example, an epidural needle inserted between vertebrae. The steerability of the stimulation lead 300 may be improved by reinforcing the distal area of the lead with a reinforcing member.

The reinforcing member may be provided within the distal portion of the lead. FIG. 4A is a lateral cross-sectional view of one embodiment of a distal end of an electrical stimulation lead 300 with a reinforcing member 450 disposed in a central lumen 404 of the lead. The lead 300 has a lead body 410 with the central lumen 404 extending along the longitudinal length of the lead body. The lead 300 includes electrodes 434 disposed along the distal end of the lead body and terminals (e.g., 210 in FIG. 2A and 236 of FIG. 2B) disposed along the proximal end of the lead body. The lead 300 also includes a number of conductors (e.g., 420 in FIG. 3B), each conductor electrically coupling at least one of the electrodes 434 to at least one of the terminals. The electrodes, terminals, and conductors are described in more detail above.

In at least some embodiments, such as those illustrated in FIGS. 4A-4C, 5, and 6A-6B, the lead 300 includes a tubular reinforcing member 450 disposed in the central lumen 404 of the lead body, preferably entirely within the distal portion of the lead. The reinforcing member 450 is provided to stiffen the portion of the distal end of the lead in which the reinforcing member 450 resides.

Preferably, the reinforcing member 450 extends distally from a location proximal of the electrodes 434. In some embodiments, such as those illustrated in FIGS. 4A, 4C, and 5, the reinforcing member 450 extends beneath one or more of the electrodes 434. For example, the reinforcing member 450 may extend beneath one of the electrodes or less than half of the electrodes, or half of the electrodes, or more than half of the electrodes. As illustrated in FIG. 4C, the reinforcing member may extend beneath all of the electrodes. The reinforcing member may even extend to the distal tip of the lead. In other embodiments, such as the embodiment of FIG. 4B, the reinforcing member may not extend under any of the electrodes or, in other words, the reinforcing member may terminate proximal of the electrodes.

The tubular reinforcing member 450 is typically a cylindrical tube that is preferably shaped similar to the central lumen 404. In at least some embodiments, the outer diameter of the reinforcing member 450 is the same as, or within 1%, 5%, or 10%, of the outer diameter of the central lumen 404. The tubular reinforcing member 450 is preferably hollow with an internal lumen to allow a stylet 452 to pass as illustrated in FIG. 5. In some embodiments, however, the reinforcing member 450 may be solid with no internal lumen.

The reinforcing member 450 can be formed of any suitable biocompatible material including, but not limited to, metals, such as stainless steel, tungsten, Nitinol™, or the like, or polymers, such as polyurethane, polyetheretherketone (PEEK), silicone, or the like.

The reinforcing member may take any suitable form, such as a hypotube, spring-like tube, a coil, a coiled spring, or any other suitable rod-like part. In some embodiments, the hypotube or spring-like tube includes spiral cuts along its length. The pitch of the spiral cuts may be constant or may vary over the length of the tube to achieve variable flexibility. The spiral cuts can be formed by any suitable method including, but not limited to, laser cutting. A coil or spring can be coiled or formed from any suitable wire such as, but not limited to, a round wire, square wire, or any other shape of wire.

The disclosed electrical stimulation lead 300 may also be part of an electrical stimulation system (e.g., electrical stimulation system 100 of FIG. 1). The electrical simulation system may include a control module coupleable to the electrical stimulation lead 300. The electrical stimulation system may also include a lead extension coupleable to the electrical stimulation lead 300 and the control module.

As illustrated in FIG. 5, a stylet 452 may be inserted in the lead 300 to facilitate implantation. Any suitable stylet can be used including straight stylets or stylets that are curved along part or all of the length of the stylet. The stylet 452 can be formed of any suitable biocompatible material, including metals, such as stainless steel, tungsten, Nitinol™, or the like, or rigid polymers.

In some embodiments, such as the embodiment illustrated in FIGS. 6A and 6B (electrodes are not illustrated in these two Figures for clarity in illustrating operations with the stylet), the stylet 452' includes a curved distal end. When inserted into the lead 300, the curving stylet 452' can cause at least a portion of the distal end of the lead body to curve, as illustrated in FIG. 6A, to facilitate steering of the lead. The reinforcing member 450 can be used to temporarily straighten the curving stylet 452' by retracting the curving stylet 452' so that the curved distal end resides within the reinforcing member 450. In embodiment in which this feature is desirable, the reinforcing member 450 should not extend to the distal tip of the lead 300 so that the curving stylet 452' may bend the distal tip for steering purposes.

A method for implanting an electrical stimulation lead may include providing the electrical stimulation lead, inserting a stylet into the central lumen of the lead body and through the tubular reinforcing member. The method may further include implanting the electrical stimulation lead into a patient using the curved distal end of the stylet to curve at least a portion of the distal end of the electrical stimulation lead and steer the lead to a desired implantation site. In some embodiments, the stylet may be retracted so that the curved distal end is straightened within the reinforcing member during, prior to, or after steering the lead for implantation.

Figure 7A:
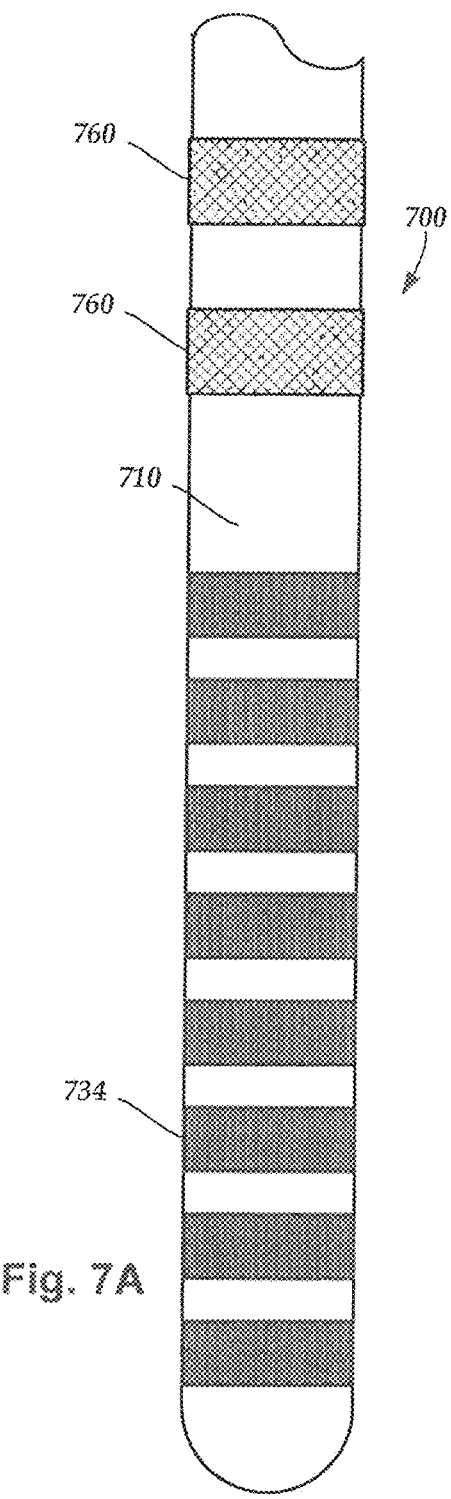
FIG. 7A is a side view of one embodiment of a distal end of a lead with reinforcing bands disposed on the lead proximal of the electrode array, according to the invention.
Figure 7B:
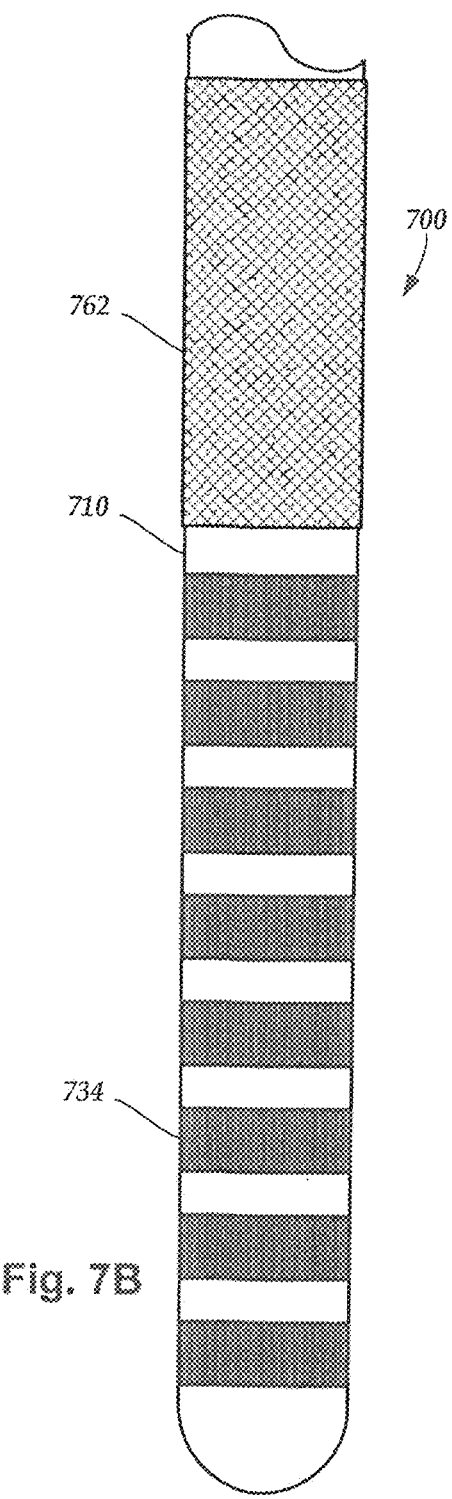
FIG. 7B is a side view of one embodiment of a distal end of a lead with a reinforcing tube disposed on the lead proximal of the electrode array, according to the invention.

In some embodiments, the distally reinforced lead may incorporate one or more reinforcing members in the form of bands or a tube arranged on the outside of the lead. FIG. 7A is a side view of an embodiment of a distal end of the lead 300 with reinforcing bands 760 disposed on a portion of the lead proximal of the electrodes 734. The reinforcing bands 760 surround portions of the distal end of the lead body 710 to stiffen the distal end of the lead. FIG. 7B is a side view of one embodiment of the distal end of the lead 700 with a reinforcing tube 762 disposed on the lead 700 proximal of the electrode array. The reinforcing bands 760 and reinforcing tube 762 should fit within an epidural needle for implantation into the patient.

The reinforcing bands 760 or reinforcing tube 762 can be formed of any suitable biocompatible material including, but not limited to, metals, such as stainless steel, tungsten, Nitinol™, or the like, or rigid polymers. The reinforcing bands or tube may take any suitable form, such as a hypotube, spring-like tube, a coil, a coiled spring, or any other suitable rod-like part. The reinforcing bands 760 may be formed on or attached to the exterior of the lead 700 using any suitable method, such as, but not limited to, swaging, crimping, compression, friction-fit, or through use of an adhesive.

Figure 8:
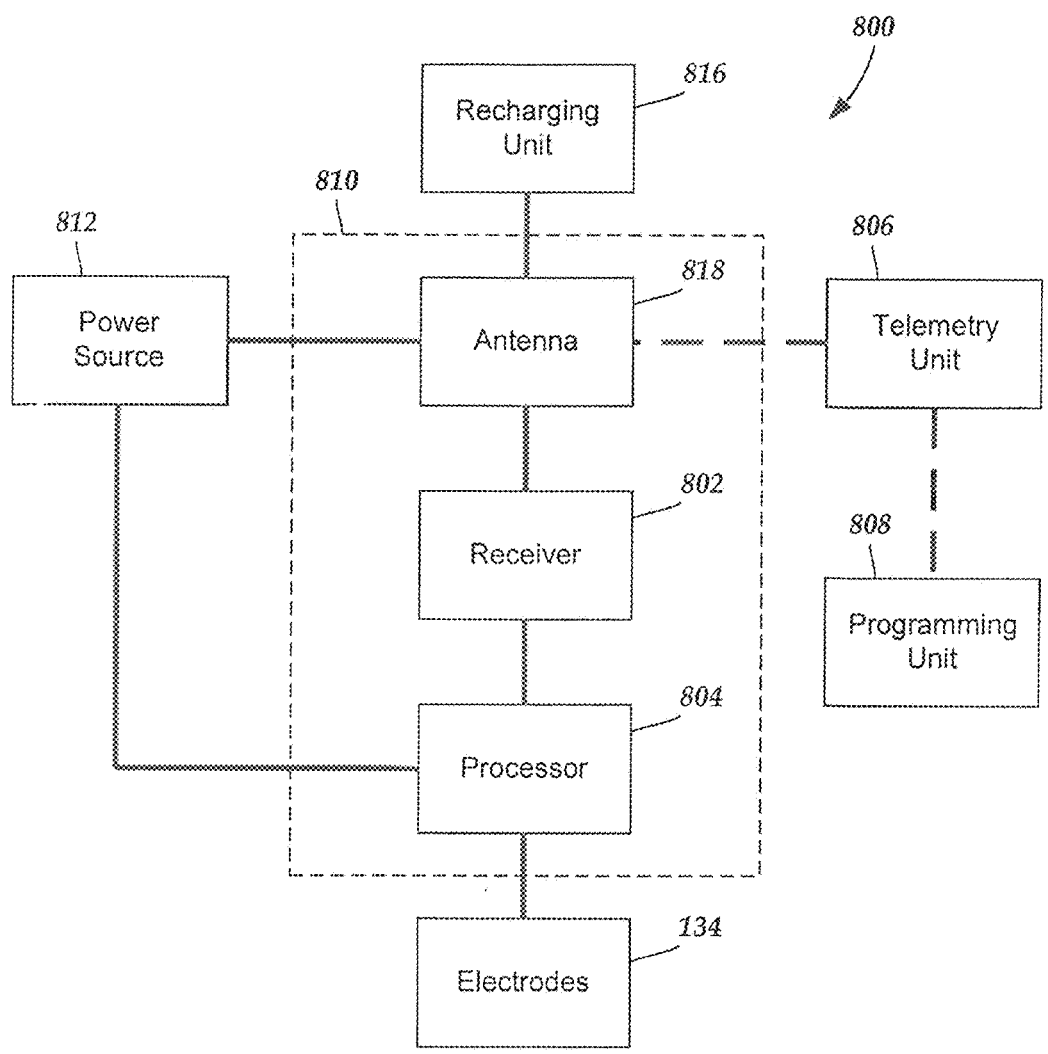
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in one or more of the stimulator references cited herein.

Some of the components (for example, power source 812, antenna 818, receiver 802, and processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in one or more of the references identified above.

In one embodiment, electrical current is emitted by the electrodes 134 on the paddle or lead body to stimulate nerve fibers, muscle fibers, or other body tissues near the electrical stimulation system. A processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 may select which electrode(s) are cathodes and which electrode(s) are anodes. In some embodiments, the processor 804 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802, which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806, which is programmed by a programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include an antenna 818 or receiver 802, and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the present invention. Since many embodiments of the present invention can be made without departing from the spirit and scope of the present invention, the present invention also resides in the claims hereinafter appended.

What is claimed as new and desired to be protected by Letters Patent of the United States is:

1. An electrical stimulation lead, comprising:
   a lead body having a distal end, a proximal end, and a longitudinal length, the lead body defining a central lumen extending along the longitudinal length of the lead body;
   a plurality of electrodes disposed along the distal end of the lead body,
   a plurality of terminals disposed along the proximal end of the lead body,
   a plurality of conductors, each conductor electrically coupling at least one of the electrodes to at least one of the terminals;
   a tubular reinforcing member disposed in the central lumen of the lead body entirely within the distal end of the lead body, the reinforcing member extending proximal of the plurality of electrodes and extending beneath no more than half of the electrodes, wherein the reinforcing member is configured and arranged to stiffen a portion of the distal end of the lead body in which the reinforcing member resides; and
   a stylet configured and arranged for insertion within the central lumen and passing through the tubular reinforcing member, wherein the stylet comprises a curved distal end that is configured and arranged, when inserted into the lead, to cause at least a portion of the distal end of the lead body, distal to the tubular reinforcing member, to curve, wherein the stylet is further configured and arranged so that the curved distal end is temporarily straightened when the stylet is retracted so that the curved distal end resides within the tubular reinforcing member.

2. The electrical stimulation lead of claim 1, wherein the reinforcing member is entirely disposed proximal of the plurality of electrodes.

3. The electrical stimulation lead of claim 1, wherein the reinforcing member extends beneath at least one of the plurality of electrodes.

4. The electrical stimulation lead of claim 1, wherein the reinforcing member comprises a hypotube.

5. The electrical stimulation lead of claim 4, wherein the hypotube is spiral cut along a length of the hypotube.

6. The electrical stimulation lead of claim 5, wherein the spiral cut varies in pitch along the length of the hypotube.

7. The electrical stimulation lead of claim 1, wherein the reinforcing member is a coiled wire.

8. An electrical stimulation system, comprising
the electrical stimulation lead of claim 1; and
a control module coupleable to the electrical stimulation lead.

9. The electrical stimulation system of claim 8, further comprising a lead extension coupleable to the electrical stimulation lead and the control module.

10. An electrical stimulation lead comprising:
a lead body having a distal end, a proximal end, an exterior, and a longitudinal length;
a plurality of electrodes disposed along the distal end of the lead body,
a plurality of terminals disposed along the proximal end of the lead body,
a plurality of conductors, each conductor electrically coupling at least one of the electrodes to at least one of the terminals; and
at least one reinforcing member disposed upon the exterior of the distal end of the lead body proximal of the plurality of electrodes, wherein the at least one reinforcing member is configured and arranged to stiffen a portion of the distal end upon which the at least one reinforcing member is disposed, wherein the at least one reinforcing member comprises a reinforcing tube having a length greater than a length of any one of the plurality of electrodes.

11. The electrical stimulation lead of claim 10, wherein the reinforcing member has a length greater than a combined length of at least four of the plurality of electrodes.

12. The electrical stimulation lead of claim 10, wherein the at least one reinforcing member is formed of metal.

13. An electrical stimulation system, comprising
the electrical stimulation lead of claim 10; and
a control module coupleable to the electrical stimulation lead.

14. An electrical stimulation lead comprising:
a lead body having a distal end, a proximal end, an exterior, and a longitudinal length;
a plurality of electrodes disposed along the distal end of the lead body,
a plurality of terminals disposed along the proximal end of the lead body,
a plurality of conductors, each conductor electrically coupling at least one of the electrodes to at least one of the terminals: and
at least one reinforcing member disposed upon the exterior of the distal end of the lead body proximal of the plurality of electrodes, wherein the at least one reinforcing member is configured and arranged to stiffen a portion of the distal end upon which the at least one reinforcing member is disposed, wherein the at least one reinforcing member comprises a plurality of reinforcing bands attached to the distal end of the lead body.

15. A method of implanting an electrical stimulation lead, the method comprising:
providing the electrical stimulation lead of claim 1;
inserting the stylet into the central lumen of the lead body and through the tubular reinforcing member; and
implanting the electrical stimulation lead into a patient using the curved distal end of the stylet to curve at least a portion of the distal end of the lead body and steer the lead to a desired implantation site.

16. The method of claim 15, further comprising retracting the curved distal end of the stylet into the tubular reinforcing member to temporarily straighten the curved distal end of the stylet.

* * * * *